United States Patent
Gonzalez-Hernandez

(10) Patent No.: US 10,299,939 B2
(45) Date of Patent: May 28, 2019

(54) BONE JOINT REPLACEMENT AND REPAIR ASSEMBLY AND METHOD OF REPAIRING AND REPLACING A BONE JOINT

(71) Applicant: TOBY ORTHOPAEDICS, INC., Miami, FL (US)

(72) Inventor: Eduardo Gonzalez-Hernandez, Miami, FL (US)

(73) Assignee: TOBY ORTHOPAEDICS, INC., Miami, FL (US)

( * ) Notice: Subject to any disclaimer, the term of this patent is extended or adjusted under 35 U.S.C. 154(b) by 0 days.

(21) Appl. No.: 15/668,043

(22) Filed: Aug. 3, 2017

(65) Prior Publication Data

US 2017/0325971 A1    Nov. 16, 2017

Related U.S. Application Data

(62) Division of application No. 13/663,129, filed on Oct. 29, 2012, now Pat. No. 9,730,797.
(Continued)

(51) Int. Cl.
  *A61F 2/46*    (2006.01)
  *A61F 2/38*    (2006.01)
  (Continued)

(52) U.S. Cl.
  CPC .............. *A61F 2/4612* (2013.01); *A61F 2/30* (2013.01); *A61F 2/3804* (2013.01); *A61F 2/389* (2013.01);
  (Continued)

(58) Field of Classification Search
  CPC .. A61F 2/46; A61F 2/4612; A61F 2/30; A61F 2/3804; A61F 2/389; A61F 2/4003;
  (Continued)

(56) References Cited

U.S. PATENT DOCUMENTS

| 1,950,799 A | 3/1934 | Jones |
| 2,500,370 A | 3/1950 | McKibbin |

(Continued)

FOREIGN PATENT DOCUMENTS

| DE | 86 28 766 U1 | 12/1986 |
| DE | 89 07 443 U1 | 9/1989 |

(Continued)

OTHER PUBLICATIONS

U.S. Appl. No. 10/993,723, filed Nov. 2004, Gonzalez-Hernandez.
(Continued)

*Primary Examiner* — Alvin J Stewart
(74) *Attorney, Agent, or Firm* — Martin & Ferraro, LLP

(57) ABSTRACT

A bone joint repair and replacement assembly. A first portion comprising a bone plate is configured to attach to a distal or proximal end of a bone proximate the joint, generally coaxially with an axis defined by the bone. A second portion comprising an articular surface is configured to attach to the first portion, generally normal with respect to the axis, and inserted into the joint. Although versions of the assembly can be configured for use with several different pivotal joints, the invention is particularly suitable for full or partial replacement of an elbow, wherein the articular surface is pivotally attached to the first portion. Another embodiment of the invention is provided to repair a fractured bone head proximate the joint, and still another embodiment of the invention is provided to repair rotator cuff-related shoulder injuries.

20 Claims, 10 Drawing Sheets

Related U.S. Application Data

(60) Provisional application No. 61/557,224, filed on Nov. 8, 2011, provisional application No. 61/552,387, filed on Oct. 27, 2011.

(51) Int. Cl.
   *A61F 2/42* (2006.01)
   *A61F 2/40* (2006.01)
   *A61F 2/30* (2006.01)

(52) U.S. Cl.
   CPC .......... *A61F 2/4003* (2013.01); *A61F 2/4202* (2013.01); *A61F 2/4261* (2013.01); *A61F 2/46* (2013.01); *A61F 2/4605* (2013.01); *A61F 2002/30471* (2013.01); *A61F 2002/30578* (2013.01); *A61F 2002/3813* (2013.01); *A61F 2002/3822* (2013.01); *A61F 2002/3827* (2013.01); *A61F 2002/4007* (2013.01); *A61F 2002/4088* (2013.01); *A61F 2002/4264* (2013.01)

(58) Field of Classification Search
   CPC .... A61F 2/4202; A61F 2/4261; A61F 2/4605; A61F 2002/4243–2002/4258; A61F 2002/3822; A61F 2002/3827; A61F 2002/3809; A61F 2002/4025; A61F 2002/4022; A61F 2002/4007
   See application file for complete search history.

(56) References Cited

U.S. PATENT DOCUMENTS

| | | | |
|---|---|---|---|
| 2,555,291 A | 5/1951 | Poupitch | |
| 2,580,821 A | 1/1952 | Toufick | |
| 2,682,265 A | 6/1954 | Collison | |
| 2,853,114 A | 9/1958 | Barry | |
| 2,875,663 A | 3/1959 | Wieber | |
| 3,489,143 A | 1/1970 | Halloran | |
| 3,552,389 A | 1/1971 | Allgower et al. | |
| 3,579,831 A | 5/1971 | Stevens et al. | |
| 3,716,050 A | 2/1973 | Johnston | |
| 3,791,380 A | 2/1974 | Dawidowski | |
| 3,824,995 A | 7/1974 | Getscher | |
| 3,900,025 A | 8/1975 | Barnes, Jr. | |
| 4,029,091 A | 6/1977 | von Bezold | |
| 4,263,904 A | 4/1981 | Judet | |
| 4,385,404 A * | 5/1983 | Sully | A61F 2/4241 128/898 |
| 4,467,479 A * | 8/1984 | Brody | A61B 17/562 128/898 |
| 4,535,768 A | 8/1985 | Hourahane et al. | |
| 4,683,878 A | 8/1987 | Carter | |
| 4,733,654 A | 3/1988 | Marino | |
| 4,776,330 A | 10/1988 | Chapman et al. | |
| 4,790,302 A | 12/1988 | Colwill et al. | |
| 4,794,919 A | 1/1989 | Nilsson | |
| 4,796,612 A | 1/1989 | Reese | |
| 4,838,264 A | 6/1989 | Bremer et al. | |
| 4,858,602 A | 8/1989 | Seidel et al. | |
| 4,870,957 A | 10/1989 | Goble et al. | |
| 4,988,350 A * | 1/1991 | Herzberg | A61B 17/746 606/65 |
| 5,003,969 A | 4/1991 | Azer et al. | |
| 5,015,248 A | 5/1991 | Burstein et al. | |
| 5,041,113 A | 8/1991 | Biedermann et al. | |
| 5,041,114 A | 8/1991 | Chapman et al. | |
| 5,108,449 A | 4/1992 | Gray | |
| 5,180,383 A | 1/1993 | Haydon | |
| 5,190,544 A | 3/1993 | Chapman et al. | |
| 5,197,966 A * | 3/1993 | Sommerkamp | A61B 17/8061 606/280 |
| 5,324,291 A | 6/1994 | Ries et al. | |
| 5,356,410 A | 10/1994 | Pennig | |
| 5,364,399 A | 11/1994 | Lowery et al. | |
| 5,405,401 A * | 4/1995 | Lippincott | A61F 2/4241 623/21.15 |
| 5,423,860 A | 6/1995 | Lizardi et al. | |
| 5,437,667 A | 8/1995 | Papierski et al. | |
| 5,443,516 A | 8/1995 | Albrektsson et al. | |
| 5,458,654 A | 10/1995 | Tepic | |
| 5,462,547 A | 10/1995 | Weigum | |
| 5,472,444 A | 12/1995 | Huebner et al. | |
| 5,505,734 A | 4/1996 | Caniggia et al. | |
| 5,578,035 A | 11/1996 | Lin | |
| 5,584,835 A | 12/1996 | Greenfield | |
| 5,586,985 A | 12/1996 | Putnam et al. | |
| 5,601,553 A | 2/1997 | Trebing et al. | |
| 5,620,449 A | 4/1997 | Faccioli et al. | |
| 5,658,287 A | 8/1997 | Hofmann et al. | |
| 5,665,088 A * | 9/1997 | Gil | A61B 17/8061 606/324 |
| 5,674,222 A | 10/1997 | Berger et al. | |
| 5,676,667 A | 10/1997 | Hausman | |
| 5,681,311 A | 10/1997 | Foley et al. | |
| 5,709,686 A | 1/1998 | Talos et al. | |
| 5,749,872 A | 5/1998 | Kyle et al. | |
| 5,766,174 A | 6/1998 | Perry | |
| 5,776,194 A | 7/1998 | Mikol et al. | |
| 5,779,704 A | 7/1998 | Kim | |
| 5,785,712 A | 7/1998 | Runciman et al. | |
| 5,840,078 A | 11/1998 | Yerys | |
| 5,868,749 A | 2/1999 | Reed | |
| 5,931,839 A | 8/1999 | Medoff | |
| 5,938,664 A * | 8/1999 | Winquist | A61B 17/8085 606/283 |
| 5,976,139 A | 11/1999 | Bramlet | |
| 5,980,575 A | 11/1999 | Albrektsson et al. | |
| 6,030,389 A | 2/2000 | Wagner et al. | |
| 6,096,040 A | 8/2000 | Esser | |
| 6,149,653 A | 11/2000 | Deslauriers | |
| 6,152,927 A | 11/2000 | Farris et al. | |
| 6,200,330 B1 | 3/2001 | Benderev et al. | |
| 6,206,881 B1 | 3/2001 | Frigg et al. | |
| D443,060 S | 5/2001 | Benirschke et al. | |
| 6,270,499 B1 | 8/2001 | Leu et al. | |
| D449,692 S | 10/2001 | Michelson | |
| 6,302,887 B1 | 10/2001 | Spranza et al. | |
| 6,331,179 B1 | 12/2001 | Freid et al. | |
| 6,348,052 B1 | 2/2002 | Sammarco | |
| 6,358,250 B1 | 3/2002 | Orbay | |
| 6,364,881 B1 | 4/2002 | Apgar et al. | |
| 6,364,882 B1 | 4/2002 | Orbay | |
| 6,379,359 B1 | 4/2002 | Dahners | |
| 6,398,783 B1 | 6/2002 | Michelson | |
| 6,406,478 B1 | 6/2002 | Kuo | |
| 6,409,768 B1 | 6/2002 | Tepic et al. | |
| 6,413,259 B1 | 7/2002 | Lyons et al. | |
| 6,440,135 B2 | 8/2002 | Orbay et al. | |
| 6,468,278 B1 | 10/2002 | Muckter | |
| D469,534 S * | 1/2003 | Bryant | D24/155 |
| 6,503,281 B1 * | 1/2003 | Mallory | A61B 17/8061 623/22.11 |
| 6,572,620 B1 | 6/2003 | Schon et al. | |
| 6,620,195 B2 | 9/2003 | Goble et al. | |
| 6,623,486 B1 | 9/2003 | Weaver et al. | |
| 6,663,669 B1 | 12/2003 | Reiley | |
| 6,669,701 B2 | 12/2003 | Steiner et al. | |
| 6,695,844 B2 | 2/2004 | Bramlet et al. | |
| 6,706,046 B2 | 3/2004 | Orbay et al. | |
| 6,712,820 B2 | 3/2004 | Orbay | |
| 6,712,856 B1 * | 3/2004 | Carignan | A61B 17/1764 623/20.35 |
| 6,719,759 B2 | 4/2004 | Wagner et al. | |
| 6,730,090 B2 | 5/2004 | Orbay et al. | |
| 6,776,781 B1 | 8/2004 | Uwaydah | |
| 6,863,671 B1 | 3/2005 | Strobel et al. | |
| 6,866,665 B2 | 3/2005 | Orbay | |
| 6,916,323 B2 | 7/2005 | Kitchens | |
| 6,945,973 B2 | 9/2005 | Bray | |
| 7,001,388 B2 | 2/2006 | Orbay et al. | |
| 7,063,701 B2 | 6/2006 | Michelson | |
| 7,128,744 B2 | 10/2006 | Weaver et al. | |

(56) References Cited

U.S. PATENT DOCUMENTS

| | | | |
|---|---|---|---|
| D536,453 S | 2/2007 | Young et al. | |
| 7,220,246 B2 | 5/2007 | Raulerson | |
| 7,229,444 B2 | 6/2007 | Boyd | |
| 7,229,445 B2 | 6/2007 | Hayeck et al. | |
| 7,235,079 B2 | 6/2007 | Jensen et al. | |
| 7,354,441 B2 | 4/2008 | Frigg | |
| 7,500,983 B1 | 3/2009 | Kaiser et al. | |
| 7,544,209 B2 * | 6/2009 | Lotke | A61F 2/3877 623/20.18 |
| 7,563,263 B2 | 7/2009 | Orbay et al. | |
| 7,582,107 B2 | 9/2009 | Trail et al. | |
| 7,591,823 B2 | 9/2009 | Tipirneni | |
| 7,604,657 B2 | 10/2009 | Orbay et al. | |
| 7,637,908 B1 | 12/2009 | Gonzalez-Hernandez | |
| 7,651,517 B2 | 1/2010 | Konieczynski et al. | |
| 7,655,029 B2 * | 2/2010 | Niederberger | A61B 17/8061 606/280 |
| 7,695,472 B2 | 4/2010 | Young | |
| 7,708,781 B2 * | 5/2010 | Scheker | A61F 2/3804 623/20.11 |
| 7,722,653 B2 | 5/2010 | Young et al. | |
| 7,740,648 B2 | 6/2010 | Young et al. | |
| 7,744,638 B2 | 6/2010 | Orbay | |
| 7,776,076 B2 | 8/2010 | Grady, Jr. et al. | |
| 7,780,667 B2 | 8/2010 | Watanabe et al. | |
| 7,780,710 B2 | 8/2010 | Orbay et al. | |
| 7,896,886 B2 | 3/2011 | Orbay et al. | |
| 7,909,859 B2 | 3/2011 | Mosca et al. | |
| 7,914,532 B2 | 3/2011 | Shaver et al. | |
| 7,927,341 B2 | 4/2011 | Orbay et al. | |
| 7,938,850 B2 | 5/2011 | Orbay et al. | |
| 7,951,176 B2 * | 5/2011 | Grady, Jr. | A61B 17/746 606/280 |
| 7,951,178 B2 | 5/2011 | Jensen | |
| 7,955,364 B2 | 6/2011 | Ziolo et al. | |
| D643,121 S | 8/2011 | Milford et al. | |
| 8,021,402 B2 | 9/2011 | Martin et al. | |
| D646,785 S | 10/2011 | Milford | |
| 8,062,296 B2 | 11/2011 | Orbay et al. | |
| 8,062,367 B2 | 11/2011 | Kirschman | |
| 8,100,953 B2 | 1/2012 | White et al. | |
| 8,182,485 B1 * | 5/2012 | Gonzalez-Hernandez | A61B 17/72 606/70 |
| 8,257,444 B2 * | 9/2012 | Linares | A61F 2/38 623/18.11 |
| 8,267,972 B1 * | 9/2012 | Gehlert | A61B 17/746 606/280 |
| 8,317,842 B2 | 11/2012 | Graham et al. | |
| 8,523,902 B2 | 9/2013 | Heaven et al. | |
| 8,545,569 B2 * | 10/2013 | Fitz | A61F 2/30756 623/20.14 |
| 8,556,946 B2 | 10/2013 | Prandi | |
| 8,574,234 B2 | 11/2013 | Gonzalez-Hernandez | |
| 8,597,362 B2 * | 12/2013 | Shenoy | A61B 17/56 623/20.21 |
| 8,597,363 B2 | 12/2013 | Liverneaux et al. | |
| 8,603,091 B2 | 12/2013 | Lutz | |
| 8,608,783 B2 | 12/2013 | Graham | |
| 8,617,242 B2 * | 12/2013 | Philipp | A61F 2/30756 623/18.11 |
| 8,728,126 B2 | 5/2014 | Steffen | |
| 8,764,808 B2 | 7/2014 | Gonzalez-Hernandez | |
| 8,906,070 B2 * | 12/2014 | Medoff | A61B 17/8004 606/280 |
| 8,961,573 B2 | 2/2015 | Gonzalez-Hernandez | |
| 9,114,016 B2 * | 8/2015 | Shenoy | A61B 17/56 |
| 9,271,772 B2 * | 3/2016 | Gonzalez-Hernandez | A61F 2/4261 |
| 9,278,004 B2 * | 3/2016 | Shenoy | A61B 17/56 |
| 9,655,727 B2 * | 5/2017 | Wellings | A61F 2/3877 |
| 9,668,868 B2 * | 6/2017 | Shenoy | A61B 17/1675 |
| 9,675,400 B2 * | 6/2017 | Katrana | A61B 17/282 |
| 9,730,797 B2 * | 8/2017 | Gonzalez-Hernandez | A61F 2/4612 |
| 9,757,240 B2 * | 9/2017 | Gonzalez-Hernandez | A61F 2/3804 |
| 9,931,136 B2 * | 4/2018 | Shenoy | A61B 17/56 |
| 9,974,582 B1 * | 5/2018 | Anissian | A61B 17/746 |
| 2002/0091391 A1 | 7/2002 | Cole et al. | |
| 2003/0135212 A1 | 7/2003 | Chow | |
| 2003/0135216 A1 | 7/2003 | Sevrain | |
| 2003/0208210 A1 | 11/2003 | Dreyfuss et al. | |
| 2004/0097939 A1 | 5/2004 | Bonutti | |
| 2004/0193277 A1 * | 9/2004 | Long | A61B 17/15 623/19.14 |
| 2004/0193278 A1 | 9/2004 | Maroney et al. | |
| 2004/0199258 A1 | 10/2004 | Macara | |
| 2004/0210220 A1 | 10/2004 | Tornier | |
| 2005/0004574 A1 | 1/2005 | Muckter | |
| 2005/0015089 A1 | 1/2005 | Young et al. | |
| 2005/0021033 A1 | 1/2005 | Zeiler et al. | |
| 2005/0038513 A1 | 2/2005 | Michelson | |
| 2005/0065612 A1 * | 3/2005 | Winslow | A61F 2/4003 623/19.14 |
| 2005/0085819 A1 | 4/2005 | Ellis et al. | |
| 2005/0182405 A1 | 8/2005 | Orbay et al. | |
| 2005/0240187 A1 | 10/2005 | Huebner et al. | |
| 2005/0267476 A1 | 12/2005 | Chervitz et al. | |
| 2005/0288681 A1 | 12/2005 | Klotz et al. | |
| 2006/0015072 A1 | 1/2006 | Raulerson | |
| 2006/0015101 A1 | 1/2006 | Warburton et al. | |
| 2006/0058795 A1 | 3/2006 | Boyd | |
| 2006/0106385 A1 | 5/2006 | Pennig | |
| 2006/0161156 A1 | 7/2006 | Orbay | |
| 2006/0217722 A1 | 9/2006 | Dutoit et al. | |
| 2006/0229623 A1 | 10/2006 | Bonutti et al. | |
| 2006/0235400 A1 | 10/2006 | Scheider | |
| 2006/0241617 A1 | 10/2006 | Holloway et al. | |
| 2006/0264947 A1 | 11/2006 | Orbay et al. | |
| 2006/0264956 A1 | 11/2006 | Orbay et al. | |
| 2006/0271105 A1 | 11/2006 | Foerster et al. | |
| 2007/0005074 A1 | 1/2007 | Chudik | |
| 2007/0016205 A1 | 1/2007 | Beutter et al. | |
| 2007/0083207 A1 | 4/2007 | Ziolo et al. | |
| 2007/0123880 A1 | 5/2007 | Medoff | |
| 2007/0123885 A1 | 5/2007 | Kirschman | |
| 2007/0162015 A1 | 7/2007 | Winquist et al. | |
| 2007/0167953 A1 | 7/2007 | Prien et al. | |
| 2007/0233113 A1 | 10/2007 | Kaelblein | |
| 2007/0233114 A1 | 10/2007 | Bouman | |
| 2007/0233115 A1 | 10/2007 | Sixto et al. | |
| 2007/0265631 A1 | 11/2007 | Fox | |
| 2008/0015591 A1 * | 1/2008 | Castaneda | A61B 17/1728 606/86 A |
| 2008/0015593 A1 | 1/2008 | Pfefferle et al. | |
| 2008/0045960 A1 | 2/2008 | Bruecker et al. | |
| 2008/0119895 A1 * | 5/2008 | Manceau | A61B 17/8042 606/280 |
| 2008/0132955 A1 * | 6/2008 | Frigg | A61B 17/8014 606/280 |
| 2008/0140130 A1 * | 6/2008 | Chan | A61B 17/1728 606/280 |
| 2008/0154311 A1 | 6/2008 | Staeubli | |
| 2008/0161853 A1 | 7/2008 | Arnold et al. | |
| 2008/0161860 A1 | 7/2008 | Ahrens et al. | |
| 2008/0161863 A1 | 7/2008 | Arnold et al. | |
| 2008/0195217 A1 * | 8/2008 | Scheker | A61F 2/3804 623/20.11 |
| 2008/0221577 A1 | 9/2008 | Elghazaly | |
| 2008/0234749 A1 | 9/2008 | Forstein | |
| 2008/0234752 A1 | 9/2008 | Dahners | |
| 2008/0249572 A1 | 10/2008 | Tandon | |
| 2009/0012571 A1 | 1/2009 | Perrow et al. | |
| 2009/0024173 A1 | 1/2009 | Reis, Jr. | |
| 2009/0048681 A1 | 2/2009 | Vlachos | |
| 2009/0069851 A1 | 3/2009 | Gillard | |
| 2009/0076554 A1 | 3/2009 | Huebner et al. | |
| 2009/0088846 A1 * | 4/2009 | Myung | A61F 2/30756 623/14.12 |
| 2009/0105838 A1 | 4/2009 | Russo et al. | |

(56) References Cited

U.S. PATENT DOCUMENTS

| | | |
|---|---|---|
| 2009/0118769 A1 | 5/2009 | Sixto, Jr. |
| 2009/0125070 A1 | 5/2009 | Sixto, Jr. et al. |
| 2009/0171399 A1 | 7/2009 | White et al. |
| 2009/0192550 A1 | 7/2009 | Leung et al. |
| 2009/0216270 A1 | 8/2009 | Humphrey |
| 2009/0228010 A1 | 9/2009 | Gonzalez-Hernandez et al. |
| 2009/0254089 A1 | 10/2009 | Tipirneni et al. |
| 2009/0254189 A1 | 10/2009 | Scheker |
| 2009/0264936 A1 | 10/2009 | Gonzalez-Hernandez |
| 2009/0275987 A1 | 11/2009 | Graham et al. |
| 2009/0275991 A1 | 11/2009 | Medoff |
| 2009/0281577 A1 | 11/2009 | Graham et al. |
| 2009/0281578 A1 | 11/2009 | Spencer |
| 2009/0299369 A1 | 12/2009 | Orbay et al. |
| 2009/0306711 A1 | 12/2009 | Stone et al. |
| 2009/0312758 A1 | 12/2009 | Petit |
| 2009/0312760 A1 | 12/2009 | Forstein et al. |
| 2009/0312802 A1 | 12/2009 | Dasilva |
| 2009/0326591 A1* | 12/2009 | Spencer, Jr. ........ A61B 17/8061 606/282 |
| 2010/0030276 A1 | 2/2010 | Huebner et al. |
| 2010/0049260 A1* | 2/2010 | Long ..................... A61B 17/15 606/86 R |
| 2010/0057086 A1 | 3/2010 | Price et al. |
| 2010/0057216 A1* | 3/2010 | Gannoe ................ A61F 2/4202 623/21.18 |
| 2010/0094358 A1 | 4/2010 | Moore |
| 2010/0145339 A1 | 6/2010 | Steffen |
| 2010/0145397 A1 | 6/2010 | Overes et al. |
| 2010/0198258 A1 | 8/2010 | Heaven et al. |
| 2010/0198354 A1* | 8/2010 | Halbrecht .............. A61B 17/58 623/20.19 |
| 2010/0217393 A1 | 8/2010 | Theofilos |
| 2010/0262194 A1 | 10/2010 | Wagner et al. |
| 2010/0274245 A1 | 10/2010 | Gonzalez-Hernandez |
| 2010/0324602 A1 | 12/2010 | Huebner et al. |
| 2010/0331844 A1 | 12/2010 | Ellis et al. |
| 2011/0029095 A1 | 2/2011 | Cartillier |
| 2011/0035020 A1 | 2/2011 | Laughner |
| 2011/0152943 A1 | 6/2011 | Gonzalez-Hernandez |
| 2011/0230919 A1* | 9/2011 | Alleyne ............ A61B 17/8061 606/286 |
| 2011/0230972 A1* | 9/2011 | Katrana ................ A61F 2/3804 623/20.11 |
| 2011/0295324 A1 | 12/2011 | Donley |
| 2012/0041564 A1 | 2/2012 | Landon |
| 2012/0083848 A1 | 4/2012 | Gonzalez-Hernandez |
| 2012/0109322 A1* | 5/2012 | Gonzalez-Hernandez ................. A61B 17/80 623/19.14 |
| 2012/0197305 A1 | 8/2012 | Gonzalez-Hernandez |
| 2012/0197308 A1 | 8/2012 | Gonzalez-Hernandez |
| 2012/0226321 A1 | 9/2012 | Gonzalez-Hernandez |
| 2012/0226322 A1 | 9/2012 | Gonzalez-Hernandez |
| 2012/0226323 A1 | 9/2012 | Gonzalez-Hernandez |
| 2012/0271366 A1* | 10/2012 | Katrana ............. A61B 17/282 606/86 R |
| 2013/0096629 A1* | 4/2013 | Rollinghoff ............ A61B 17/80 606/281 |
| 2013/0116734 A1 | 5/2013 | Gonzalez-Hernandez |
| 2013/0150977 A1* | 6/2013 | Gabriel ................ A61F 2/3859 623/20.32 |
| 2013/0289627 A1 | 10/2013 | Gonzalez-Hernandez |
| 2013/0338780 A1 | 12/2013 | Berchoux et al. |
| 2014/0121709 A1* | 5/2014 | Gonzalez-Hernandez ................. A61F 2/4003 606/286 |
| 2014/0172020 A1 | 6/2014 | Gonzalez-Hernandez |
| 2014/0180344 A1 | 6/2014 | Gonzalez-Hernandez |
| 2014/0277177 A1 | 9/2014 | Gonzalez-Hernandez |
| 2015/0045898 A1 | 2/2015 | Gonzalez-Hernandez |
| 2015/0164566 A1 | 6/2015 | Gonzalez-Hernandez |
| 2018/0116807 A1* | 5/2018 | Lenich ................ A61F 2/30771 |

FOREIGN PATENT DOCUMENTS

| | | |
|---|---|---|
| DE | 43 43 117 A1 | 6/1995 |
| DE | 198 57 279 A1 | 6/2000 |
| DE | 299 07 161 U1 | 8/2000 |
| EP | 0 551 588 A1 | 11/1992 |
| EP | 1 132 052 A2 | 9/2001 |
| EP | 1 468 655 A2 | 10/2004 |
| FR | 2 606 268 A1 | 5/1988 |
| FR | 2 680 673 A1 | 3/1993 |
| FR | 2 712 173 A1 | 5/1995 |
| JP | 4-138152 A | 5/1992 |
| WO | WO 99/38448 A1 | 8/1999 |
| WO | WO 02/071963 A1 | 9/2002 |
| WO | WO 2005/037117 A1 | 4/2005 |
| WO | WO 2008/007194 A2 | 1/2008 |
| WO | WO 2008/007196 A2 | 1/2008 |
| WO | WO 2012/003884 | 1/2012 |

OTHER PUBLICATIONS

U.S. Appl. No. 11/079,350, filed Mar. 2005, Gonzalez-Hernandez.
U.S. Appl. No. 11/366,676, filed Mar. 2006, Gonzalez-Hernandez.
U.S. Appl. No. 11/493,122, filed Jul. 2006, Gonzalez-Hernandez.
U.S. Appl. No. 11/526,331, filed Sep. 2006, Gonzalez-Hernandez.
U.S. Appl. No. 11/707,775, filed Feb. 2007, Gonzalez-Hernandez.
Acumed; ACU-LOC Wrist Plating System; Jul. 2009; 20 pages.
Acumed; The Mayo Clinic Congruent Elbow Plates (catalog); 2003; 19 pages.
Acumed; The Mayo Clinic Congruent Elbow Plate System (catalog); Apr. 2006; 20 pages.
Christie, J., C.R. Howie and P.C. Armour, Fixation of displaced subcapital femoral fractures. Compression screw fixation versus double divergent pins. *J Bone Joint Surg* [*Br*]1988; 70-B: 199-201.
Cross, W.M. et al., "Achieving stable fixation: biomechanical designs for fracture healing," AAOS Now (2008) 3 pages.
Guha, AR, et al.; "A New Technique of Fixation of Radial Head Fractures Using a Modified Tubular Plate," Journal of Postgraduate Medicine; Jul. 2004; vol. 50, Issue 2; pp. 113-114; Accessed Aug. 6, 2008 at: http://www.jpgmonline.com/article.asp?issn=0022-3859;year=2004;volume=50;issue=2;spage=113;epage=114;aulast=Guha.
Hand Innovations, LLC; DVR Anatomic, Volar Plating System; 2007; 4 pages.
Hussain M., R.N. Natarajan, A.H. Fayyazi, B.R. Braaksma, G.B. Andersson and H.S. An, *Screw angulation affects bone-screw stresses and bone graft load sharing in an anterior cervical corpectomy fusion with a rigid screw-plate construct: a finite element model study*; Spine Journal, vol. 9, Issue 12; Dec. 2009; pp. 1016-1023 (published online Oct. 12, 2009).
Lakatos, R. et al.; "General principles of internal fixation"; eMedicine; Aug. 2006; 51 pages.
"MIS Technique," published by Zimmer®, 1 page, prior to Nov. 19, 2004.
Postak, Paul D.; "Biomechanical Properties of Fixed-Angle Volar Distal Radius Plates Under Dynamic Loading;" 2007; 6 pages.
Robert, III, K.Q., R. Chandler, R,V, Barratta, K.A. Thomas and M.B. Harris, The effect of divergent screw placement on the initial strength of plate-to-bone fixation. *J Trauma*. Dec. 2003;55(6):1139-44.
Synthes, "Large Fragment LCP Instrument and Implant Set;" technique guide; 2003; 31 pages.
Synthes; 3.5 mm LCP Periarticular Proximal Humerus Plate; Apr. 2010; 22 pages.
Synthes; Locking Compression Plate (LCP) System (brochure); 2003; 6 pages.
Synthes, "Locking Compression Plate (LCP) System. Locking screw technology and conventional plating in one system;" 2003; 6 pages.
Synthes; Locking Compression Plate (LCP) System (brochure); Jan. 2007; 6 pages.
Synthes; Modular Mini Fragment LCP System (brochure); 2007; 12 pages.

(56) References Cited

OTHER PUBLICATIONS

Synthes; Small Fragment Locking Compression Plate (LCP) System (brochure); 2002; 43 pages.
Written Opinion of the International Searching Authority; International Application No. PCT/US2009/036211; dated Sep. 23, 2010; 8 pages.
"Zimmer® Universal Locking System," The Journal of Bone and Joint Surgery, vol. 89, No. 7, Jul. 2007, 1 page.
Zimmer, Inc. "Zimmer® Universal Locking System," brochure (2006), 4 pages.
Zimmer, Inc.; "Zimmer Universal Locking System;" brochure; 2009, 2 pages.
Zimmer, Inc. "Zimmer Holdings to Launch Innovative Locking Plate System at Orthopaedic Trauma Association Meeting," Sep. 14, 2006; 3 pages.
Zimmer, Inc.; "Zimmer Small Fragment Universal Locking System;" Surgical Technique; 2010; 16 pages.
Zimmer; Zimmer Periarticular Plating System-Low-Profile Fixation (catalog); 2003; 8 pages.

\* cited by examiner

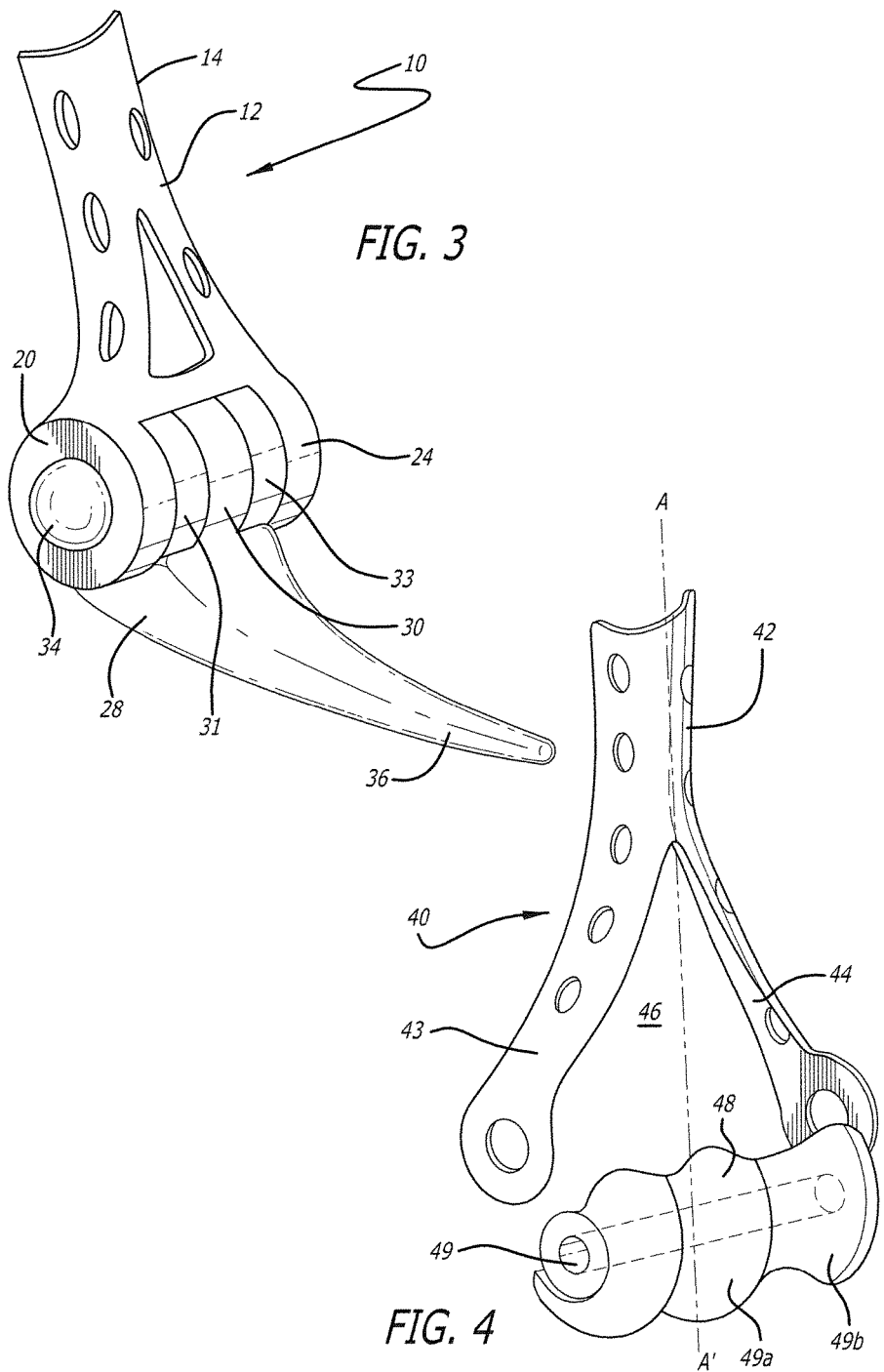

BONE JOINT REPLACEMENT AND REPAIR ASSEMBLY AND METHOD OF REPAIRING AND REPLACING A BONE JOINT

DESCRIPTION OF THE INVENTION

The present invention is a divisional of U.S. application Ser. No. 13/663,129, filed Oct. 29, 2012; which claims the benefit of Provisional Application No. 61/552,387, filed Oct. 27, 2011, and of Provisional Application No. 61/557,224, filed Nov. 8, 2011, all of the contents of which are incorporated herein by reference.

FIELD OF THE INVENTION

The present invention broadly relates to assemblies used in the repair and replacement of pivotal bone joints. More particularly, the present invention relates to assemblies for replacement and partial replacement of elbows, joint repair implants for other relatively small pivotal joints such as wrists, ankles, and knees, repair of fractured bone heads proximate joints, and implants for repair of shoulder rotator cuff injuries.

BACKGROUND OF THE INVENTION

Inserting implants and replacing pivotal bone joints, particularly relatively small joints such as elbows, wrists, ankles, and knees, is a difficult process due to the relatively complex configuration of such joints. While all pivotal bone joints are defined by an intersection and cooperation of proximal and distal heads of different bones, held together by a plurality of ligaments, relatively smaller pivotal joints, such as elbows, wrists, ankles, and knees have a large number of bones, including a large number of relatively fine bones, the heads of which have many different configurations. Designing a replacement joint, a partial replacement joint, or a repair implant, against which proximal and distal heads with different configurations can articulate smoothly presents a complex task for joint repair and replacement implant manufacturers and for orthopedic surgeons.

For example, an elbow comprises a junction of three different bones, the heads of which have different configurations. An upper arm, or humerus, has a distal end, comprising a trochlea and a capitellum, defining one part of the elbow. A forearm, comprising two bones, a radius and an ulna, have proximal heads, defining another part of the elbow. The proximal head of the ulna includes, on one side a coronoid process, and on an opposite side, an extending olecranon, which cooperate to define a trochlear notch. A trochlea of the distal end of the humerus pivots in this trochlear notch. In addition, a medullary cavity is an elongated narrow cavity in the ulna storing bone marrow. The shape, surface roughness, and proper articulation of all of these bone components must be considered when designing a suitable elbow replacement or partial replacement assembly. In addition to the heads of these bones, the elbow includes soft tissue, e.g., ligaments, collagen fibers, and so forth must be accounted for when designing a suitable replacement or partial replacement assembly.

Similar issues arise when designing repair or replacement implants for pivotal joints such as wrists, ankle, and knees, which likewise are defined by cooperation of proximal and distal heads of a plurality of bones, ligaments, and other soft tissue.

For these and other reasons, it is common in the field when patients experience damage to pivotal joints, resulting, e.g., from over-work, hyper-extension, falling, or playing contact sports, to treat the pain, e.g., with pain-killers, heat and cold, and external supports, rather than by repairing or replacing the joint.

Another type of problem can occur with a shoulder joint when a patient experiences an injury to a rotator cuff. Like other joints, the shoulder is defined by cooperation of proximal and distal heads of several bones, e.g., a proximal head of a humerus, a distal head of a clavicle, a Glenoid Socket, and an A.C. socket. Soft tissue includes, among others, a group of muscles and tendons known as a rotator cuff, which stabilizes the shoulder. A natural upper surface of the humeral head is smooth, and acts as a gliding surface between the humeral head and the rotator cuff. The rotator cuff, however, is subject to damage resulting from, e.g., over-work, sudden violent movements, attempting to lift an overly-heavy weight, playing contact sports, and so forth. Motion of an injured rotator cuff across the head of the humerus can be painful. Moreover, if the rotator cuff injury is severe or not repaired promptly, a condition known as rotator cuff arthropathy may occur, i.e., formation of an arthritic rough area on the humeral head. Movement of soft tissue across this rough bone surface is even more painful.

There is a need for improved assemblies in the field of elbow repair and replacement, repair implants for other pivotal joints, and assemblies for repair of rotator cuff injuries, including but not limited to rotator cuff arthropathy.

SUMMARY OF THE INVENTION

Accordingly, the present invention is directed to bone joint replacement and repair assemblies that substantially obviate one or more of the problems caused by the limitations and disadvantages of the related art.

An elbow replacement assembly in accordance with the present invention includes a first component, including a plate portion configured for attachment to a distal end of a humerus, a generally annular first lobe extending from the plate portion, defining a first aperture therein, and a generally annular second lobe extending from the plate portion, spaced from the first lobe, defining a second aperture therein, and a second component including a generally annular head defining a third aperture therein, insertable between the first and second lobes, the first, second, and third apertures substantially aligning to define a channel, and a pivot pin insertable into the channel to define a pivotal hinge.

The second component further includes one of a stem portion and a plate portion projecting away from the generally annular head portion. The stem portion can be configured for insertion into a medullary cavity of an ulna associated with the elbow, and the plate portion can be configured for attachment to the exterior of the ulna.

A partial elbow replacement assembly in accordance with another aspect of the present invention includes a plate portion configured for attachment to a distal end of a humerus, the humerus defining an axis, the plate portion positioned substantially coaxially with the axis, an end of the bone plate including first and second spaced apart lobes defining a yoke portion, and an articular portion pivotally attachable between the first and second lobes of the yoke portion, oriented generally transverse to the axis, to define a portion of the elbow.

In the partial elbow replacement assembly, the articular portion is configured to include at least one of an artificial capitellum and an artificial trochlea, and is configured to be received in a trochlear notch of an ulna.

A bone joint repair implant assembly in accordance with another aspect of the invention includes a first portion defining a plate portion, configured for attachment to one of a distal end of a bone proximate the joint and a proximal end of a bone proximate the joint, the bone defining an axis and the plate portion positioned substantially coaxially with the axis, the plate portion having an end portion positioned proximate the joint, and a second portion attached to the end portion of the plate portion, generally normal with respect to the axis, extending into the joint to define an articular surface. Preferably, a buttress portion is provided between the first portion and the second portion to support the articular surface.

In the aspect of the present invention described above, the implant may be configured for a wrist, with the plate portion configured for attachment to a distal end of a radius, and the articular surface configured as an articular surface for at least one of the plurality of bones cooperating to define the wrist. Alternatively, the implant may be configured for a knee, with the plate portion configured for attachment to a proximal end of a tibia, and the articular surface configured as an articular surface for at least one of the plurality of bones cooperating to define the knee. Alternatively, the implant may be configured for an ankle, with the plate portion configured for attachment to a distal end of the tibia, and the articular surface configured as an articular surface for at least one of the bones cooperating to define the ankle. In one embodiment, when the implant is configured for a wrist, the buttress may be configured to raise the articular surface to a position spaced away from the end portion of the plate portion.

A bone repair assembly for repairing a fractured proximal head of a bone, e.g., a radius, in accordance with another aspect of the present invention, includes a plate portion configured for attachment to a proximal neck of the bone, the bone defining an axis, and the plate portion positioned substantially coaxially with the axis, and a generally circular cap portion projecting generally normal to the plate portion across the fractured head of the bone.

The generally circular cap portion can be either hollow or solid. Preferably, when the bone head is fractured into a plurality of jagged fractured bone pieces, the cap portion includes a peripheral edge, with an annular skirt portion depending from the peripheral edge to substantially surround the fractured bone pieces. Fasteners can penetrate the skirt portion to fix the fractured bone pieces in place under the cap.

A shoulder joint rotator cuff repair assembly, in accordance with another aspect of the present invention includes a plate portion configured for attachment to a proximal end of a humerus, and a prosthetic articular portion extending from the plate portion, configured to cover a surface portion on the proximal end of the humerus and a humeral head. In addition, the prosthetic articular portion is configured to cover a surface portion of the humerus and of the humeral head damaged as a result of rotator cuff arthropathy. The prosthetic articular portion defines a gliding surface between the humeral head and the rotator cuff. In an alternate embodiment, an artificial gliding surface also can be attached to and undersurface of an acromion proximate the humeral head.

It is to be understood that both the foregoing general description and the following detailed description are exemplary and explanatory, and are intended to provide a written description of the invention set forth in the claims.

The accompanying drawings, which are incorporated in and constitute a part of this specification, illustrate presently preferred embodiments of the invention and together with the description, serve to explain the principles of the invention.

BRIEF DESCRIPTION OF THE DRAWINGS

FIG. 3 is a perspective view of a fully-assembled elbow replacement assembly depicted in FIG. 2;

FIG. 4 is a perspective exploded-parts view of a partial elbow replacement assembly in accordance with the present invention;

DESCRIPTION OF THE PREFERRED EMBODIMENTS

Reference will now be made in detail to the present preferred embodiments of the invention, example of which are illustrated in the accompanying drawings. Wherever possible, the same reference numbers will be used throughout the drawings to refer to the same or like parts.

Figure 1:
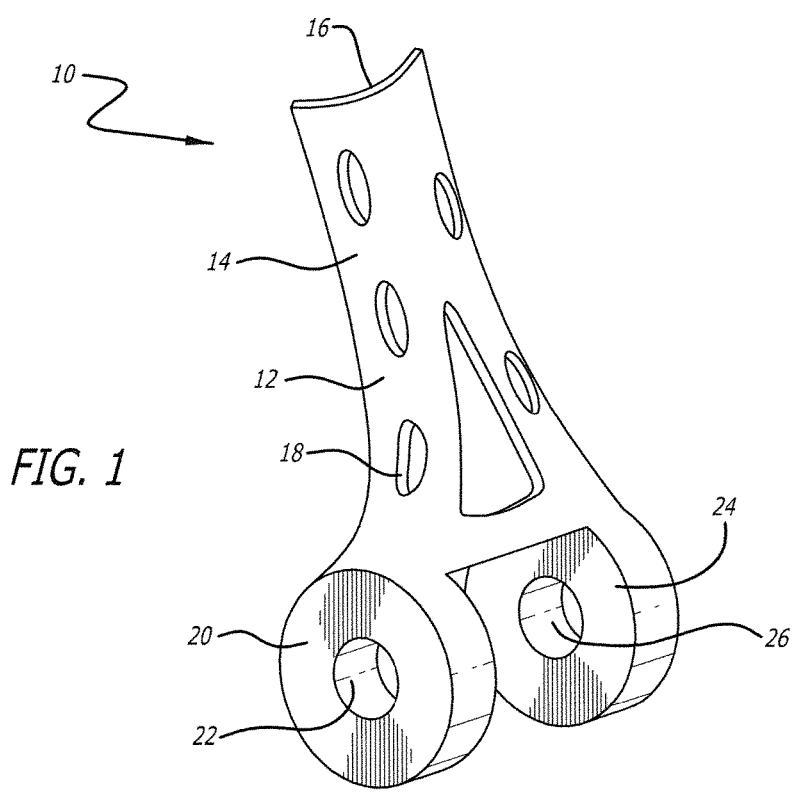
FIG. 1 is a perspective view of a first component of an elbow replacement assembly in accordance with the present invention.
Figure 2:
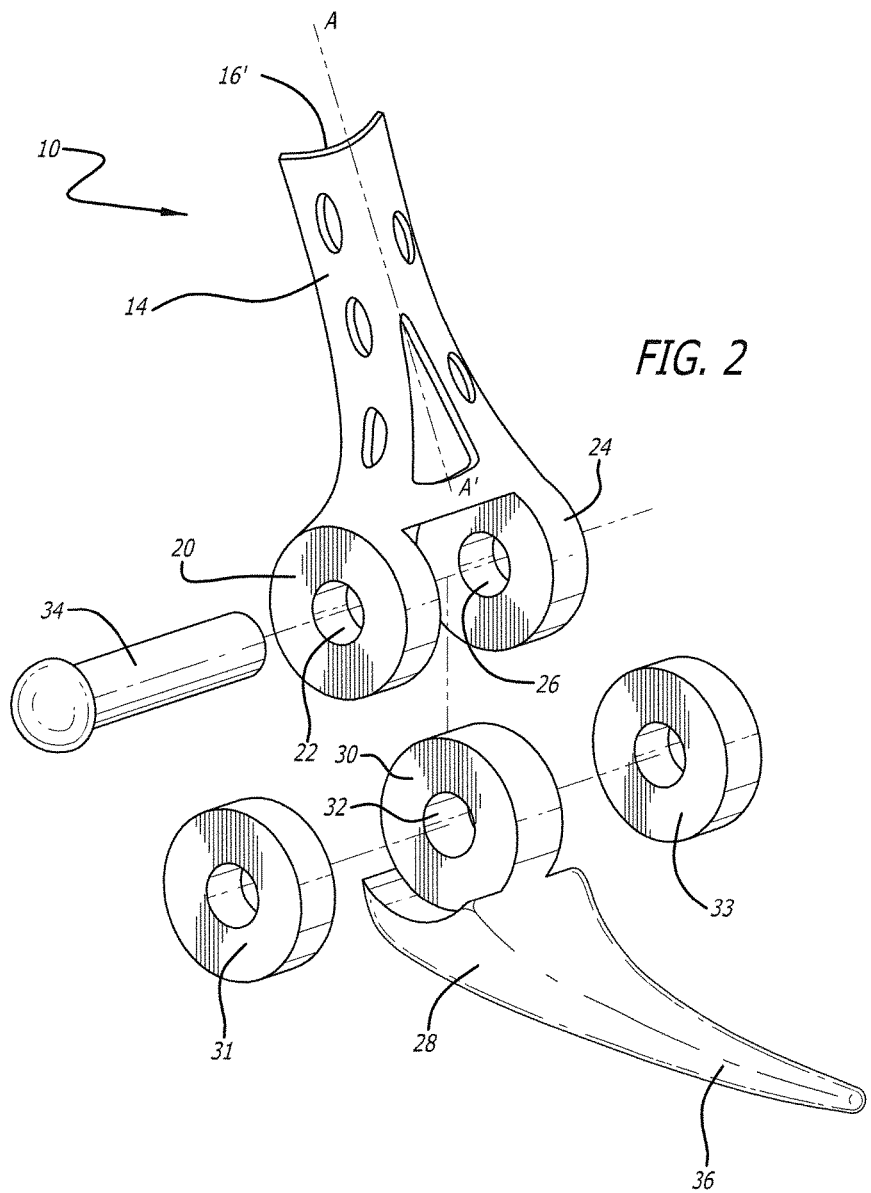
FIG. 2 is a perspective exploded-parts view of an elbow replacement assembly in accordance with the present invention.

An exemplary embodiment of an elbow replacement assembly of the present invention is shown in FIGS. 1-3, and designated generally by reference numeral 10. As embodied herein, and referring to FIGS. 1-3, the elbow replacement assembly 10 includes a first component 12. The first component 12 includes a plate portion 14, which is configured with a rear arcuate face 16, and at least one aperture 18, dimensioned for insertion therethrough of appropriate fasteners, for attachment of the plate portion 14 to a distal end of a humerus. First component 12 further includes a generally annular first lobe 20, defining a first aperture 22 therein, and a generally annular second lobe 24, spaced from the first lobe 20, defining a second aperture 26 therein.

Referring to FIGS. 1-3, the elbow replacement assembly 10 further includes a second component 28. Second component 28 includes a generally annular head portion 30, defining a third aperture 32 therein. The head portion 30 inserts between the first and second annular lobes 20 and 24, such that the apertures 22, 32, and 26 substantially align with one another to define a channel. Annular bushings or washers 31 and 33 also may be inserted in the aligned channel. A pivot pin 34 inserts into the channel to define a pivotal hinge. The second component 28 also includes a tapering tip portion 36, projecting away from the head portion 30. The tip portion 36 is configured to be inserted in a medullary cavity of an ulna associated with the elbow. Alternately, rather than including the tip portion 36 for insertion into the medullary cavity of the ulna, the second component could include a plate portion projecting away from the head portion 30. Such a plate portion could be configured for attachment to the exterior of the ulna.

Replacement of an elbow with the elbow replacement assembly of FIGS. 1-3 includes surgically preparing the elbow for implant of the elbow replacement assembly 10; attaching the plate portion 14 to a respective distal end of a humerus substantially coaxially with an axis A-A' defined by the humerus, with first and second spaced annular lobes 20 and 24 extending proximate the distal end of the humerus; inserting annular head 30 between the first and second lobes 20 and 24; inserting the pivot pin 34 into the channel defined by the aligned apertures 22, 32, and 26 to define a pivotal hinge; and inserting the tip portion 36 in the medullary cavity of the ulna associated with the elbow, thereby defining a complete elbow replacement assembly.

Figure 5:
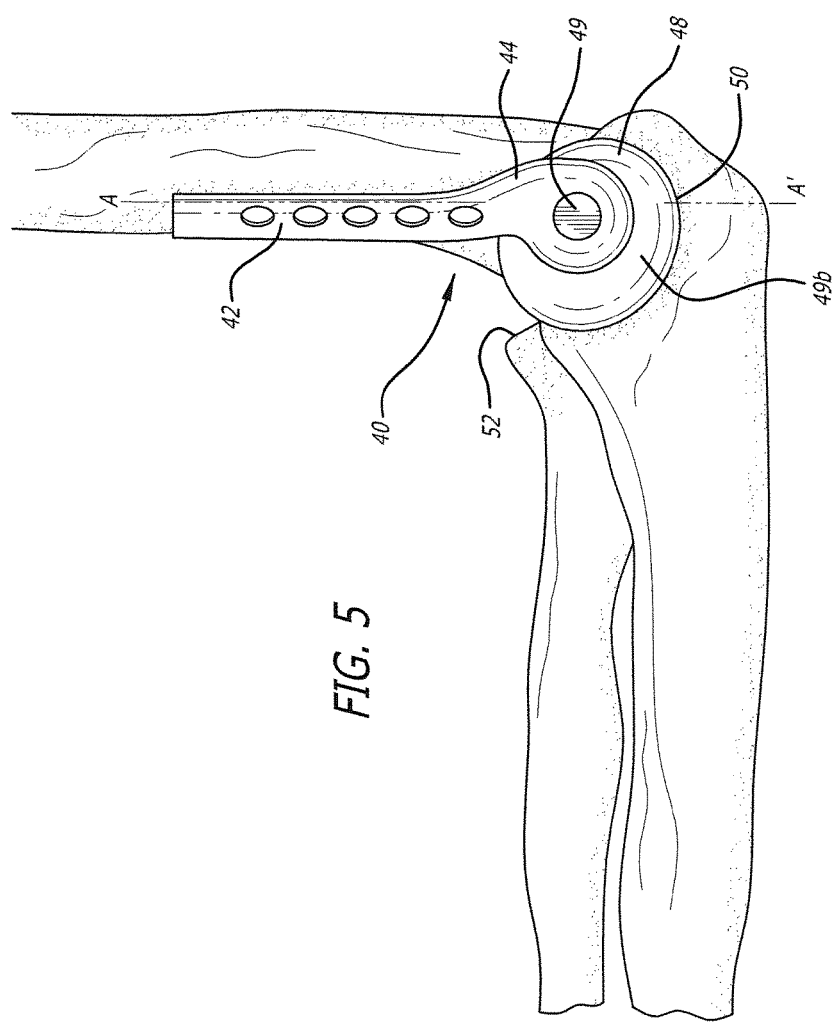
FIG. 5 is a side view of an assembled partial joint replacement assembly in accordance with the invention pivotally mounted in a trochlear notch of an ulna.

An exemplary embodiment of a partial elbow replacement assembly in accordance with the invention is shown in FIGS. 4-5, and is designated generally by reference numeral 40. A partial elbow replacement also is disclosed in U.S. application Ser. No. 13/282,810, the contents of which are incorporated herein by reference. As broadly embodied in FIGS. 4-5, the partial elbow replacement assembly 40 includes a bone plate 42, configured for attachment to a distal end of a humerus, substantially coaxially with an axis A-A' defined by the humerus. A distal end of bone plate 42 proximate the elbow joint separates into first and second spaced-apart lobes 43 and 44, defining a yoke portion 46. An artificial prosthetic articular portion 48 is pivotally attachable with a pivot pin (not shown) between the first and second lobes 43 and 44 through an aperture 49 formed in the prosthetic articular portion 48, at an angle α generally transverse to the axis A-A'. Preferably, prosthetic articular portion 48 is made of a relatively strong, corrosion-resistant metal, e.g., titanium, or a suitable strong, corrosion-resistant nickel-alloy.

As broadly embodied in FIGS. 4 and 5, the prosthetic articular portion 48 is configured to replace at least one of a natural capitellum and trochlea associated with the distal end of the humerus in the elbow. The prosthetic portion 48 includes an artificial capitellum portion 49a and an artificial trochlea portion 49b. In addition, as depicted in FIG. 5, the prosthetic articular portion 48 is configured to pivot in a trochlear notch 50 of the ulna, and articulate with respect to a radial head 52 of the radius. In doing so, the prosthetic articular portion 48 serves as a portion of the ulnotrochlear joint and a portion of the radiocapitellar joint.

Figure 6:
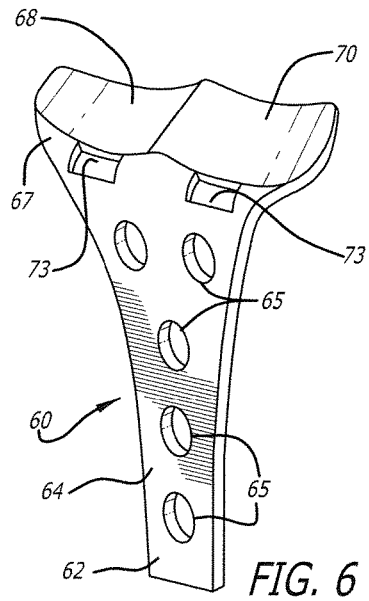
FIG. 6 is a rear perspective view of a bone joint repair implant assembly in accordance with the present invention.
Figure 7:
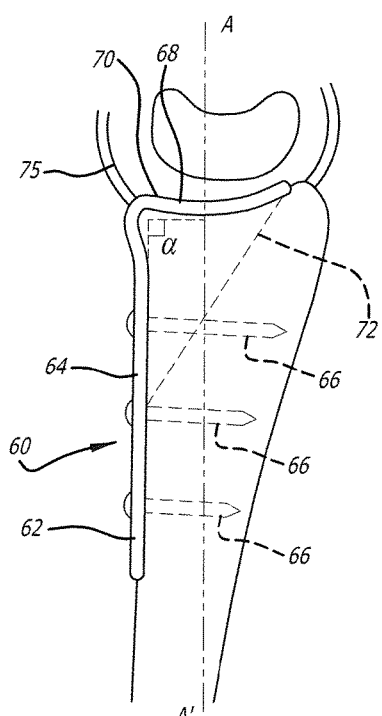
FIG. 7 is a side view of the bone joint repair implant assembly of FIG. 6 mounted in a bone joint.
Figure 8:
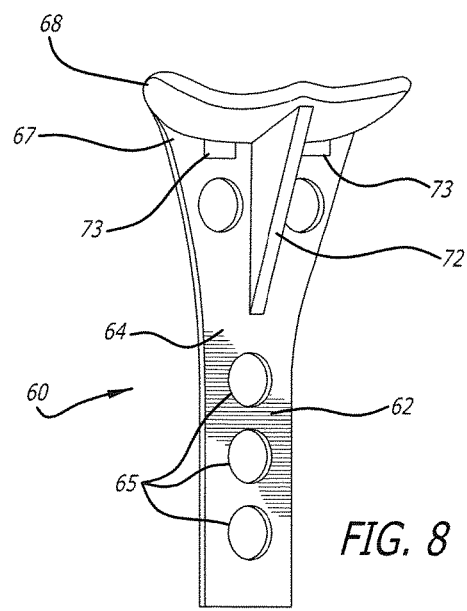
FIG. 8 is a front perspective view of the bone joint repair implant assembly of FIG. 6.

An exemplary embodiment of a bone joint repair implant assembly in accordance with another aspect of the present invention is depicted in FIGS. 6-8, and designated generally by the reference numeral 60. As broadly embodied in FIGS. 6-8, bone joint repair implant assembly 60 includes a first portion 62 defining a plate portion 64, configured with a plurality of apertures 65 dimensioned to receive fasteners 66 (FIG. 6) therethrough for attachment of the plate portion 64 to a neck of a respective bone proximate either a distal end of the bone, or a proximal end of the bone, depending on the particular joint to which the bone joint repair implant assembly 60 is to be attached. The respective bone defines an axis A-A', and the plate portion 64 is positioned substantially coaxially with the axis A-A' proximate the respective joint.

Referring to FIGS. 6-8, the bone joint repair implant assembly 60 further includes a second portion 68 attached to an end portion 67 of the plate portion 64, at an angle α generally normal to the axis A-A'. The second portion 68 is configured to extend into the joint to define an articular surface 70. Articular surface 70 is made of a metal such as titanium, or another suitable bone implant material. As further embodied in FIGS. 6 and 8, in the case of a wrist implant, the articular surface 70 comes into contact with a surface of a volar capsule 75. Preferably, a plurality of openings 73 are defined in the plate portion 64 at the end portion 67. The openings 73 allow for repair of the volar capsule 75 to, for example, bone of a distal end of a radius.

Preferably, bone joint repair implant assembly 60 includes an articular surface support. As broadly embodied in FIGS. 7-8, the articular surface support is defined by a buttress 72 inserted between the first portion 62 and the second portion 68, to provide support to the articular surface 70.

Referring to FIG. 7, because of the need to implant the buttress 72, one of ordinary skill in the art will understand that implantation of bone joint repair assembly 60 requires additional surgical preparation of the end of the respective bone proximate the joint prior to attachment of the implant.

Figure 9:
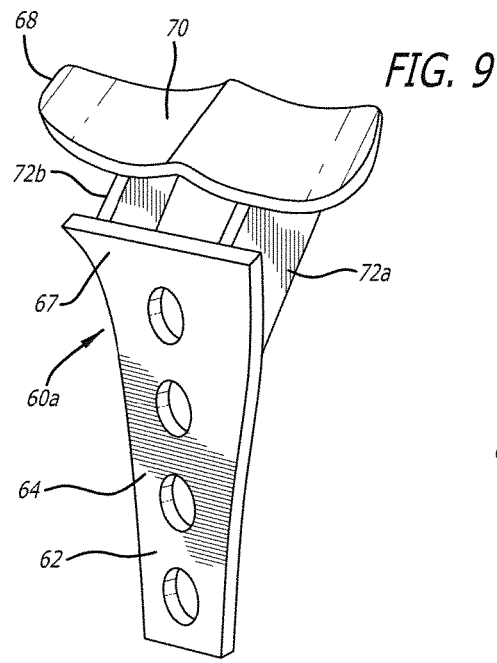
FIG. 9 is a rear perspective view of another embodiment of a bone joint implant in accordance with the present invention.
Figure 11:
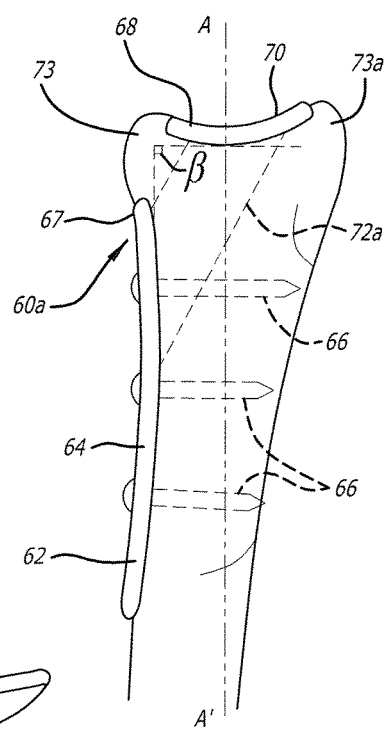
FIG. 11 is a side view of the bone joint repair implant assembly of FIG. 9 mounted in a bone joint.
Figure 10:
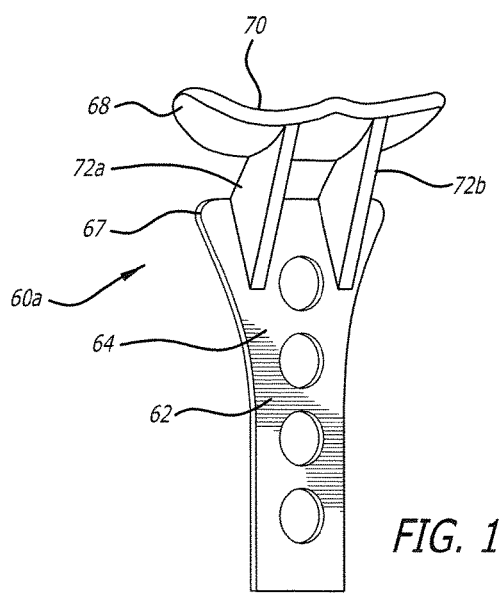
FIG. 10 is a front perspective view of the bone joint repair implant assembly of FIG. 9.

FIGS. 9-11 broadly depict an alternate embodiment 60a of the bone joint repair implant assembly of FIGS. 6-8. In the alternate embodiment 60a of FIGS. 9-11, two buttresses 72a and 72b are provided between the first portion 62 and the second portion 68, supporting articular portion 70 at an angle β with respect to the first portion 62. As broadly depicted in FIG. 11, in the case of a wrist implant, the buttresses 72a and 72b also are configured and positioned to lift the articular portion 70 up to a position spaced away from the end 67 of the first portion 62, so that a volar rim 73 and a dorsal rim 73a do not come in contact with the metal implant. The volar rim 73, and the dorsal rim 73a, therefore, are not covered by the second portion 68, thereby allowing the volar rim 73 and the distal rim 73a to contact soft tissue. One of ordinary skill will understand that use of the alternate embodiment 60a of the bone joint repair implant repair assembly of FIGS. 9-11 will require additional surgical preparation of the respective joint for insertion of the two buttresses 72a and 72b.

The bone joint repair implant assemblies 60 and 60a described above, and broadly depicted in FIGS. 6-11, can be used with several different pivotal joints, including, but not limited to knees, ankles, and wrists. In the case of a knee, the plate portion 64 is configured for attachment to a proximal end of a tibia, and the articular surface 70 is configured as an articular surface for at least one of the plurality of bones defining the knee. In an alternate embodiment, when the joint is an ankle, the plate portion 64 is configured for attachment to a distal end of a tibia, and the articular surface 70 is configured as an articular surface for at least one of a plurality of bones defining the ankle. In yet another alternate embodiment, when the joint is a wrist, the plate portion 64 is configured for attachment to a distal end of a radius, and the articular surface 70 is configured as an articular surface for at least one of a plurality of bones defining the wrist. A bone joint implant replacement assembly similar in function to bone joint replacement implant assemblies 60 and 60a is disclosed in U.S. application Ser. No. 13/663,209, by the same inventor, being filed concurrently herewith, the contents of which are incorporated herein by reference.

Figure 12:
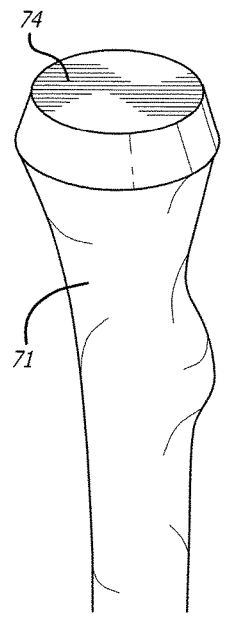
FIG. 12 is a perspective view of a proximal head of a bone, e.g., a radius.
Figure 13:
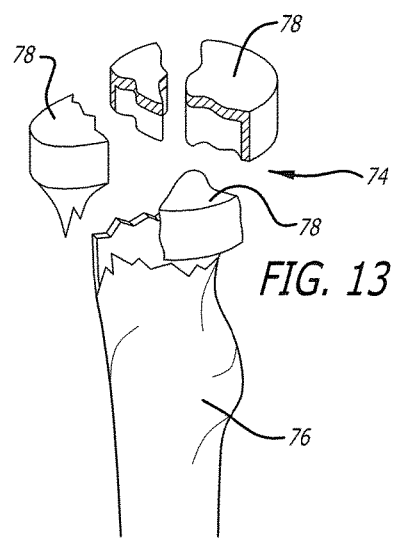
FIG. 13 is a perspective view of a proximal head of a bone, e.g., a radius fractured into a plurality of bone fragments.

In several cases, prior to implanting a repair or replacement of a bone joint, a surgeon must first repair a cracked or fractured head of one of a patient's bones cooperating to define the respective joint. This procedure is particularly essential when a head of a bone is fractured into a plurality of jagged bone fragments, which can become lodged in, and interfere with, the new artificial joint, or can interfere with ligaments and other soft tissue associated with the joint. This issue is particularly problematic in the case of a full or partial joint replacement, or in the case of insertion of a repair implant. FIG. 12 broadly depicts a proximal head 74 and a neck 76 of a proximal end of a radius associated with an elbow. Although the discussion below, and the below disclosure of the preferred embodiment of this aspect of the invention, relates to a proximal head of a radius proximate an elbow, one of ordinary skill will recognize that the bone head, and the bone head fracture assembly discussed below can be modified as necessary to apply to a head of any bone proximate a pivotal bone joint. FIG. 13 broadly depicts the proximal head 74 of the radius fractured into a plurality of jagged bone fracture pieces 78. This fractured radius head will require repair prior to insertion of an elbow replacement or partial replacement assembly, in order to provide a smooth surface to the proximal head 74 of the radius.

Figure 14:
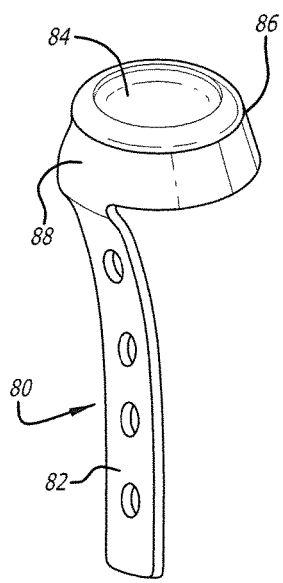
FIG. 14 is a perspective view of one embodiment of a bone repair assembly for a fractured head of a bone, e.g., a radius in accordance with the present invention.
Figures 15, 15A, 16:
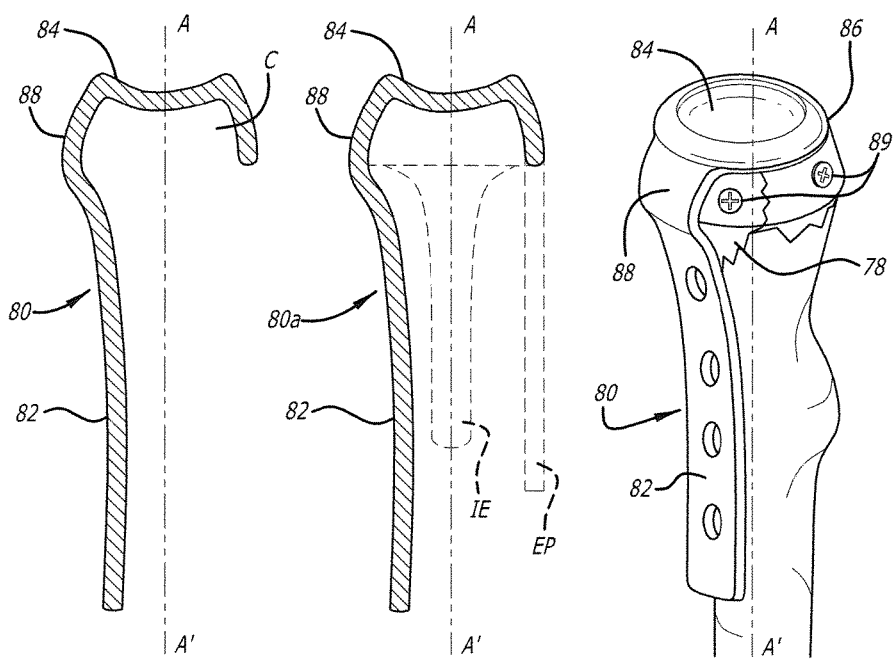
FIG. 15 is a side cross-sectional view of the bone repair assembly of FIG. 14.
FIG. 15A is a side cross-section view of another embodiment of a bone repair assembly for a fractured head of a bone, e.g., a radius, in according with the invention.
FIG. 16 is a perspective view of a bone repair assembly in accordance with the present invention installed on a fractured proximal head of a bone, e.g., a radius.

Exemplary embodiments of a bone repair assembly for repairing the fractured bone head are shown in FIGS. 14-16, and designated generally by reference numeral 80.

As embodied herein, and referring to FIG. 14, the bone repair assembly 80 for a fractured bone head, e.g., a proximal head of a radius, includes a plate portion 82 configured for attachment to the neck 76 of the bone proximate the fractured head, the bone defining an axis A-A', and the plate portion disposed generally coaxially with the axis. The plate portion 82 is configured to engage an extramedullary surface of the neck 76 of the radius. The bone repair assembly 80, in accordance with the invention, further includes a generally circular cap (or head) portion 84 projecting generally normal to the plate portion 82, across the fractured head 74 of the bone. As shown in FIG. 16, the cap portion 84 is configured to cover the fractured head 74. The entire bone repair assembly 80 may be made of an absorbable material or other non-metallic material, and the plate portion 82 and the cap portion 84 can be made of different materials. Such materials may include ceramic. Furthermore, the absorbable material may dissolve entirely or partially.

Preferably, the generally circular cap portion 84 can be either solid or hollow, with the particular embodiment chosen depending on the nature of the fracture to bone head 74, and depending on the professional judgment of the respective surgeon.

The generally circular cap portion 84 further includes a peripheral edge 86, and an annular skirt 88 depending from the peripheral edge 86, configured to substantially surround the bone fracture pieces 78. Accordingly, the cap portion 84 can include a cavity C (FIG. 15) for receiving the bone head 74 and/or the fractured bone pieces 78. As broadly depicted in the embodiment of FIG. 16, the peripheral skirt 88 can further be configured for attachment with fasteners 89 to the bone fractured bone pieces 78, in order to fix the fractured bone pieces 78 in place within the confines of the cap 84, so that the fractured bone pieces 78 will be substantially restricted from interfering with repair or replacement of the joint.

Additionally, as shown in FIG. 15A, an alternate embodiment 80a of the bone repair assembly can include an intramedullary extension IE and extension portion EP. The intramedullary extension IE extends downwardly from the cap portion 84, and is configured for receipt in the medullary cavity of the radius. Furthermore, the extension portion (or extramedullary extension) EP extends downwardly from the cap portion 84, and is configured to contact the (in similar fashion to the plate portion 82) an extramedullary surface of the neck 76 of the radius. Fasteners (not shown) can be used to join the plate portion 82, the intramedullary extension IE, the extension portion EP, and/or the neck 76 to one another.

Figure 17:
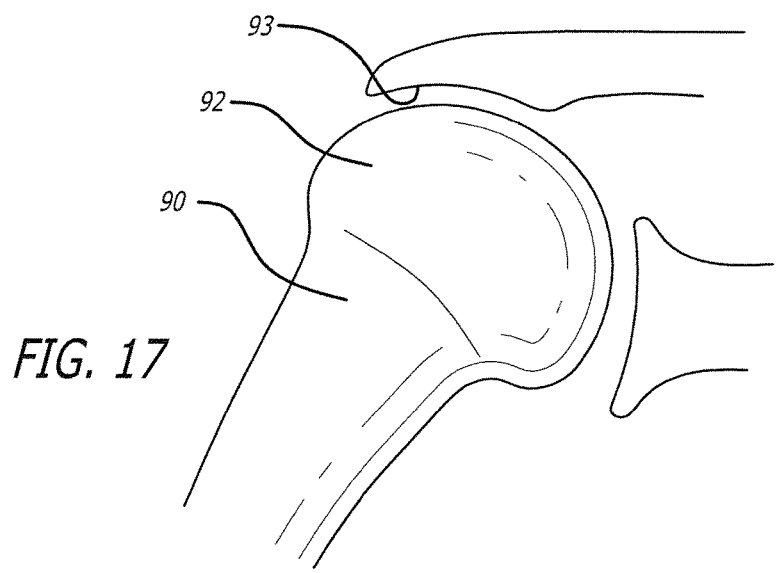
FIG. 17 is a side view broadly depicting heads of a plurality of bones cooperating to define a shoulder joint.
Figure 18:
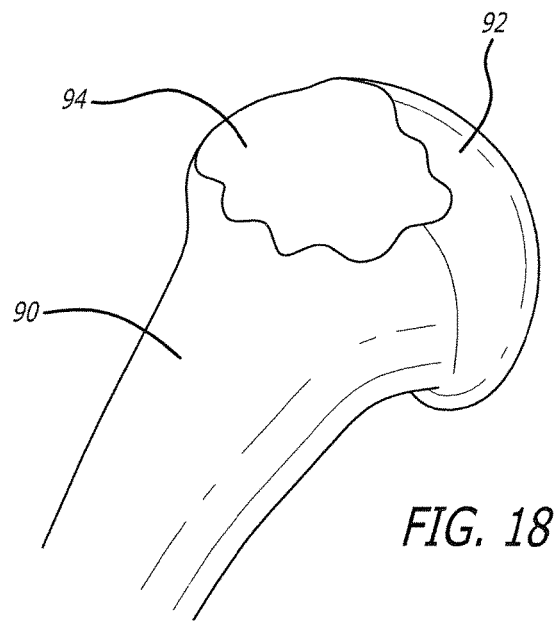
FIG. 18 is a perspective view of a proximal end of a humerus and a humeral head, with a damaged portion on a surface thereof resulting from rotator cuff arthropathy.
Figure 19:
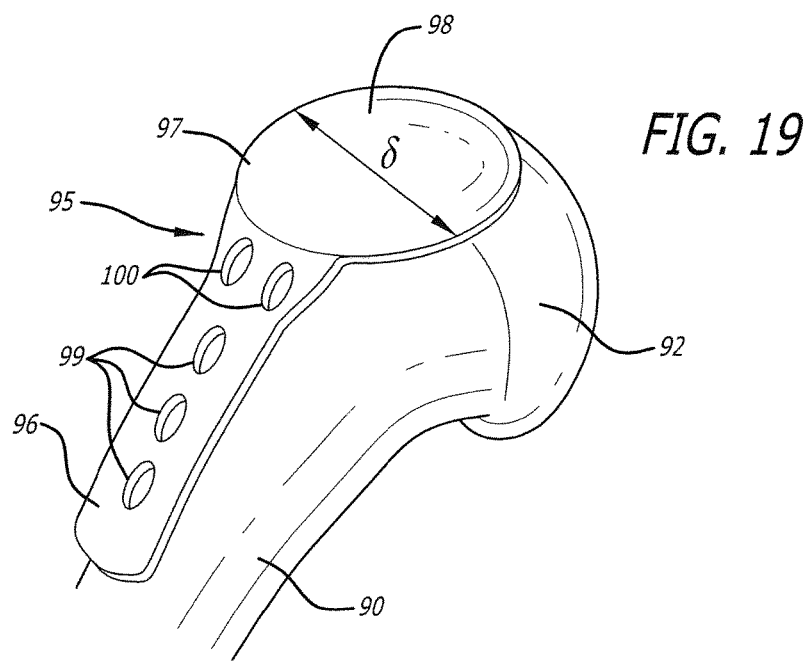
FIG. 19 is a perspective view of a shoulder joint rotator cuff repair assembly in accordance with the invention, in contact with the proximal end of the humerus and the humeral head of FIG. 18.
Figure 20:
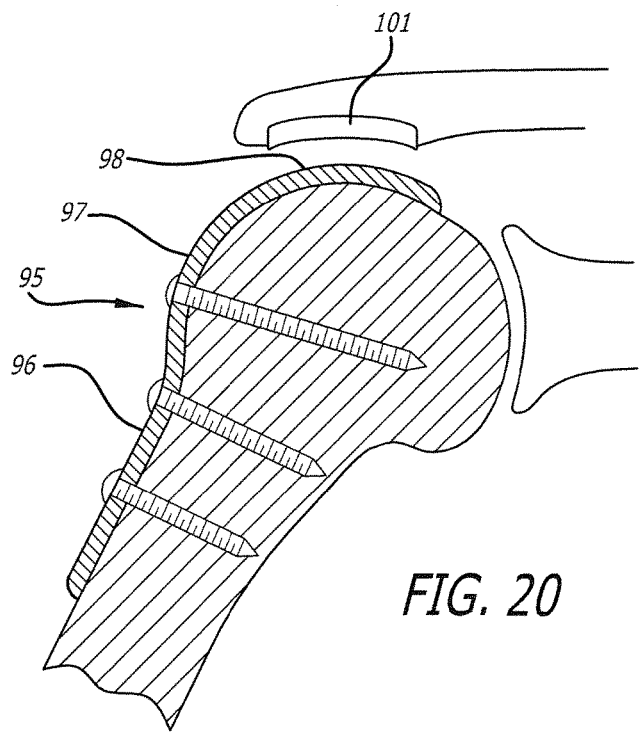
FIG. 20 is a side partial cross-sectional view of the shoulder joint of FIG. 18, with the shoulder joint rotator cuff repair assembly in accordance with the invention attached to the proximal end and humeral head thereof.

In another aspect of the present invention, FIGS. 19-20 broadly depict an assembly for the repair of injuries to a shoulder joint, particularly rotator cuff injuries, and rotator cuff arthropathy. FIG. 17 broadly depicts a proximal end of a humerus 90 using fasteners (not shown) received through apertures 99 and 100, and a humeral head 92 extending into an (unnumbered) shoulder joint. In addition to heads of various bones, ligaments, muscles, tendons and sockets defining the shoulder, the shoulder is further defined by the rotator cuff (not shown). FIG. 18 also broadly depicts an arthritic damaged surface 94 on a surface of the humerus 90 and the humeral head 92, commonly known as rotator cuff arthropathy, a condition which evolves over time when there is a chronic tear of the rotator cuff. The humeral head 92 subluxes proximally and articulates with an undersurface 93 of an acromion, shown in FIG. 17. Motion of the shoulder in this condition results in painful grinding between arthritic damaged surface 94 and the undersurface 93 of the acromion.

An exemplary embodiment of a rotator cuff repair assembly in accordance with the invention is shown in FIGS. 19-20, and is designated generally by reference numeral 95.

As broadly embodied in FIGS. 19-20, the rotator cuff repair assembly 95 includes a plate portion 96 attachable to a proximal end of the humerus 90 using fasteners (not shown) received through apertures 99 and 100, and a generally circular prosthetic articular portion 97 projecting from a proximal end of the plate portion 95.

Preferably, and as broadly depicted in FIG. 19, the prosthetic articular portion 97 has a diameter δ sufficient to cover the damaged portion 94 of the humeral head 92. In addition, in accordance with the invention, the prosthetic articular portion 97 is configured to act as a gliding surface 98 between the humeral head 92 and the rotator cuff. As further embodied in FIG. 20, an artificial gliding surface portion 101 may be installed on the undersurface 93 of the acromion.

Persons of ordinary skill in the art will recognize that various modifications and variations can be made to the preferred embodiment described above, without departing from the spirit or scope of the invention. The present invention covers any such modifications and variations, provided they fall within the scope of the claims and their legal equivalents.

What is claimed is:

1. A bone joint repair implant comprising:
a first portion defining at least a plate portion configured for attachment to a bone at and adjacent one of a distal end and a proximal end of the bone, the plate portion having a first end portion, an opposite second end portion, a rear surface, and a mid-longitudinal axis extending through the first end portion and the second end portion, the bone defining an axis and the plate portion being positionable with respect to the bone to substantially align the mid-longitudinal axis thereof with the axis of the bone, the first end portion of the plate portion being positionable proximate a bone joint, and the rear surface being contactable to at least a first portion of the bone; and
a second portion defining at least an articular portion having a rear surface and an articular surface, the articular portion being attached to the first end portion of the plate portion, and the articular portion being positionable into the bone joint, the rear surface being contactable to at least a second portion of the bone at and adjacent the bone joint to cover a damaged surface of the second portion of the bone, the rear surface of the articular portion being arcuate in a first plane extending through the rear surface and the articular surface of the articular portion, the rear surface of the articular portion being arcuate in a second plane extending through the rear surface and the articular surface of the articular portion that is perpendicular to the first plane, and the articular surface defining a new joint surface.

2. The bone joint repair implant of claim 1, wherein the bone joint is defined by a rotator cuff and a humeral head of a humerus, the plate portion is configured for attachment to a proximal end of a humerus, the articular portion is configured for positioning between the rotator cuff and the humerus head, and the articular surface of the articular portion is configured to define a glide surface for contacting the rotator cuff.

3. The bone joint repair implant of claim 2, wherein the rear surface of the articular portion is at least in part concave and configured to contact a portion of a humeral head.

4. The bone joint repair implant of claim 3, wherein the articular surface of the articular portion is at least in part convex.

5. The bone joint repair implant of claim 4, wherein the articular portion includes an at least in part arcuate perimeter.

6. The bone joint repair implant of claim 1, wherein the rear surface of the articular portion is at least in part concave and configured to contact a portion of a humeral head.

7. The bone joint repair implant of claim 1, wherein the articular surface of the articular portion is at least in part convex.

8. The bone joint repair implant of claim 1, wherein the articular portion includes an at least in part arcuate perimeter.

9. The bone joint repair implant of claim 1, wherein the plate portion includes a first end at a terminal end of the first end portion, a second end at a terminal end of the second end portion, and a length between the first end and the second end, the first end portion including a first maximum width perpendicular to the length and the second end portion including a second maximum width perpendicular to the length, the first maximum width being greater than the second maximum width.

10. The bone joint repair implant of claim 1, wherein the plate portion includes a first end, an opposite second end, a length between the first end and the second end, and at least two bone screw receiving holes spaced along the length of the plate portion.

11. The bone joint repair implant of claim 10, wherein the plate portion includes at least two bone screw receiving holes spaced apart from one another across a width of the plate portion perpendicular to the length thereof.

12. A bone joint repair implant comprising:
a first portion defining at least a plate portion configured for attachment to a bone at and adjacent one of a distal end and a proximal end of the bone, the plate portion having a first end portion, an opposite second end portion, a rear surface, and a mid-longitudinal axis extending through the first end portion and the second end portion, the bone defining an axis and the plate portion being positionable with respect to the bone to substantially align the mid-longitudinal axis thereof with the axis of the bone, the first end portion of the plate portion being positionable proximate a bone joint, and the rear surface being contactable to at least a first portion of the bone, the plate portion including a first end at a terminal end of the first end portion, a second end at a terminal end of the second end portion, and a length between the first end and the second end, the first end portion including a first maximum width perpendicular to the length and the second end portion including a second maximum width perpendicular to the length, the first maximum width being greater than the second maximum width; and
a second portion defining at least an articular portion having a rear surface and an articular surface, the articular portion being attached to the first end portion of the plate portion, and the articular portion being positionable into the bone joint, the rear surface being contactable to at least a second portion of the bone at and adjacent the bone joint to cover a damaged surface of the second portion of the bone, and the articular surface defining a new joint surface.

13. The bone joint repair implant of claim 12, wherein the bone joint is defined by a rotator cuff and a humeral head of a humerus, the plate portion is configured for attachment to a proximal end of a humerus, the articular portion is configured for positioning between the rotator cuff and the humerus head, and the articular surface of the articular portion is configured to define a glide surface for contacting the rotator cuff.

14. The bone joint repair implant of claim 13, wherein the rear surface of the articular portion is at least in part concave and configured to contact a portion of a humeral head.

15. The bone joint repair implant of claim 14, wherein the articular surface of the articular portion is at least in part convex.

16. The bone joint repair implant of claim 12, wherein the articular portion includes an at least in part arcuate perimeter.

17. The bone joint repair implant of claim 12, wherein the plate portion includes a first end, an opposite second end, a length between the first end and the second end, and at least two bone screw receiving holes spaced along the length of the plate portion.

18. The bone joint repair implant of claim 17, wherein the plate portion includes at least two bone screw receiving holes spaced apart from one another across a width of the plate portion perpendicular to the length thereof.

19. The bone joint repair implant of claim 12, wherein the rear surface of the articular portion is at least in part concave and configured to contact a portion of a humeral head.

20. The bone joint repair implant of claim 12, wherein the articular surface of the articular portion is at least in part convex.

* * * * *